(12) United States Patent
Allen

(10) Patent No.: US 9,149,259 B1
(45) Date of Patent: Oct. 6, 2015

(54) PATIENT SAFETY AND WELLBEING DEVICE FOR COVERING WIRES AND NEEDLES USED IN MAMMOGRAPHY OR ULTRASOUND GUIDED NEEDLE LOCALIZATION

(76) Inventor: Cynthia E. Allen, Monroeville, OH (US)

( * ) Notice: Subject to any disclaimer, the term of this patent is extended or adjusted under 35 U.S.C. 154(b) by 0 days.

(21) Appl. No.: 13/589,103

(22) Filed: Aug. 18, 2012

Related U.S. Application Data

(60) Provisional application No. 61/525,815, filed on Aug. 21, 2011.

(51) Int. Cl.
- *A61B 17/34* (2006.01)
- *A61B 10/02* (2006.01)

(52) U.S. Cl.
CPC .................................. *A61B 10/0233* (2013.01)

(58) Field of Classification Search
None
See application file for complete search history.

(56) References Cited

U.S. PATENT DOCUMENTS

| | | | | |
|---|---|---|---|---|
| 4,799,495 A | * | 1/1989 | Hawkins et al. | 600/567 |
| 4,844,061 A | * | 7/1989 | Carroll | 128/207.17 |
| 5,074,847 A | * | 12/1991 | Greenwell et al. | 604/174 |
| 5,290,266 A | * | 3/1994 | Rohling et al. | 604/272 |
| 5,795,308 A | * | 8/1998 | Russin | 600/567 |
| RE36,398 E | * | 11/1999 | Byrne et al. | 604/198 |
| 6,080,114 A | * | 6/2000 | Russin | 600/567 |
| 6,254,613 B1 | * | 7/2001 | Harrison | 606/118 |
| 7,322,360 B2 | * | 1/2008 | Fogarty et al. | 128/899 |
| 7,396,346 B2 | * | 7/2008 | Nakajima | 604/167.03 |
| 7,659,439 B2 | * | 2/2010 | Grossman | 602/57 |
| 8,663,266 B1 | * | 3/2014 | Obsuth | 606/185 |
| 2005/0090783 A1 | * | 4/2005 | Sibbitt | 604/263 |
| 2005/0197627 A1 | * | 9/2005 | Huang et al. | 604/171 |
| 2007/0282181 A1 | * | 12/2007 | Findlay et al. | 600/323 |
| 2010/0016802 A1 | * | 1/2010 | Tambourgi et al. | 604/179 |
| 2013/0289359 A1 | * | 10/2013 | Ritter et al. | 600/300 |
| 2013/0324883 A1 | * | 12/2013 | Vaillancourt et al. | 600/567 |

* cited by examiner

*Primary Examiner* — Long V Le
*Assistant Examiner* — Kevin Pontius
(74) *Attorney, Agent, or Firm* — Jerry Semer

(57) ABSTRACT

This apparatus consist of three devices. The first device is latex free radiolucent small diameter piece of tubing with a small diameter opening in its center. The wire that is protruding from the patient is run through the small diameter opening. The tubing is long enough to fully cover the sharp ends of the wire. When the tubing has been placed over the wire, it is looped in a loose loop and held to the skin by a rectangle latex free adhesive bandage which has no adhesive in its center. The third device is used when the patient is waiting for surgery and the needle and wire are left in the breast. At this point an adjustable height cup is placed over the wire. The adjustable height cup has four tabs extending from its bottom which are used to hold the cup in place on the body over the wire.

15 Claims, 13 Drawing Sheets

PATIENT SAFETY AND WELLBEING DEVICE FOR COVERING WIRES AND NEEDLES USED IN MAMMOGRAPHY OR ULTRASOUND GUIDED NEEDLE LOCALIZATION

This application is a continuation-in-part of prior applications No. 61/525,815 that was filed on Aug. 21, 2011.

FIELD OF THE INVENTION

This invention relates to the field of patient wellbeing while waiting for surgery and more particularly to the field of securing and covering the localization wires and needles for the patient's wellbeing and safety.

BACKGROUND OF THE INVENTION

In performing either Mammography or Ultrasound Guided Breast Needle Localization, a needle is placed in the breast to guide the surgeon to the correct area for biopsy. This needle has a thin wire through its center. The doctor can choose to leave both the needle and wire in the patient's breast, or remove the needle, leaving only the wire to guide the surgeon.

If only a wire is left in the breast for surgery, the wire is then later followed by the surgeon to remove the area of abnormality. The exposed ends of the wires are sharp and can hurt the patient or others. Also, if the wires are moved or bumped it can cause pain to the patient. The wire also has the chance to be accidentally displaced. One of the objectives of the invention is to develop a system that will protect the patient and others from harm due to the wires, and greatly minimize the chance of accidental displacement. If the wire is displaced, the biopsy may not be performed in the correct area of the breast.

Currently, the general practice with the wire is to attempt to cover the exposed sharp end of the wire with gauzes. Then the wires are placed against a patient's skin and held down with several pieces of tape.

This causes several problems. Gauze is not very effective in covering the exposed ends of the wires. The problem with securing the wires with gauze and tape are the possibility of accidental displacement, skin irritation from the tape and the exposed wire injuring the patient.

The inventor has produced a unique solution to solve this problem.

The features that make applicant's solution possible are that she uses a small diameter tube that is radiolucent and latex free to cover the wire. Then, to hold the wire in place the tubing is loosely looped and secured against the body with a rectangular shaped latex free adhesive bandage with a non-adhesive center. The weight and size of the tubing allows it to be looped and fit securely against the body. When held in place with the rectangular shaped latex free adhesive bandage, there is less chance of accidental displacement and eliminates the chance of the sharp end of the wire injuring the patient or others.

If the doctor chooses to leave both the needle and the wire guide in the breast, it is still necessary to cover the wire and needle. In the prior art the needles and wires are usually covered with a Dixie cup. There are several problems with this procedure. The first problem is that the needles/wires come in different lengths. Thus, the size of a Dixie cup does not properly fit all the sizes of the wires/needles. Secondly, the Dixie cups are not sanitary. Thirdly, it is difficult to securely tape the Dixie cup over the wires. Usually the tape does not adequately secure the needle and wire and individuals may be allergic to the tape or adhesive used. To solve this problem the applicant has invented a cylindrical cup like device whose height can be adjusted.

The cylindrical cup like device comes with four tabs that have adhesive on their bottom side for attaching the adjustable height cylindrical cup like device to the body.

SUMMARY OF THE INVENTION

This apparatus consist of three devices. The first device is a latex free radiolucent small diameter piece of tubing. The tubing has a small diameter opening in its center. The wire that is protruding from the patient's breast that the doctor follows to the tumor is run through the small diameter opening in the middle of the tubing. The tubing is longer then the wire and thus fully covers the wire leaving the sharp end covered by the tubing. When the tubing has been placed over the wire, it is loosely looped in a circle and held to the skin by a rectangle latex free adhesive bandage which has no adhesive in its center. The non adhesive area is placed over the loosely looped tubing and the two ends of the adhesive bandage are then placed against the skin holding the tubing against the skin.

The third piece of equipment is used if the doctor chooses to leave both the wire and the needle in the breast. At this point an adjustable height cup is placed over the wire. The adjustable height cup has four tabs extending from its bottom. The four tabs are adhesive tabs. These tabs are used to hold the cup in place on the body over the wire and needle.

DETAILED DESCRIPTION OF THE INVENTION

Figure 1:
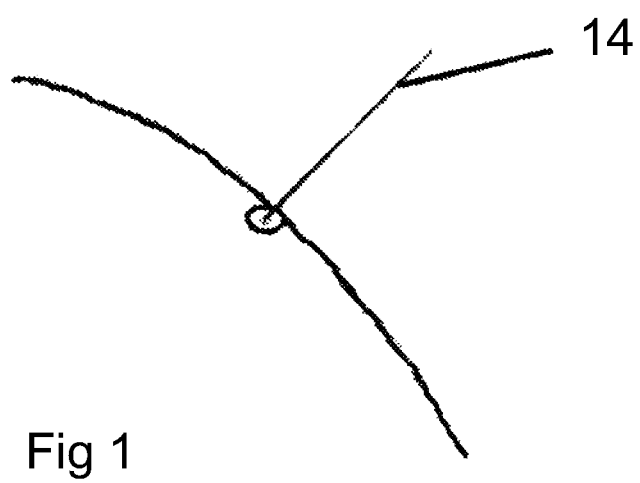
FIG. 1 is a view of a patient with a wire that is used to locate a tumor protruding from the patient's body.

FIG. 1 shows an individual with a wire 14 protruding from his/her skin. The wire 14 has been inserted by a doctor to show the location of an abnormal area to be removed by a biopsy. In the procedure of the biopsy of an abnormal area to be removed, the abnormal area is located by diagnostic equipment such as x-ray or ultrasound. A wire 14 is placed in the individual for the surgeon to follow to locate the abnormal area during surgery.

Figure 1A:
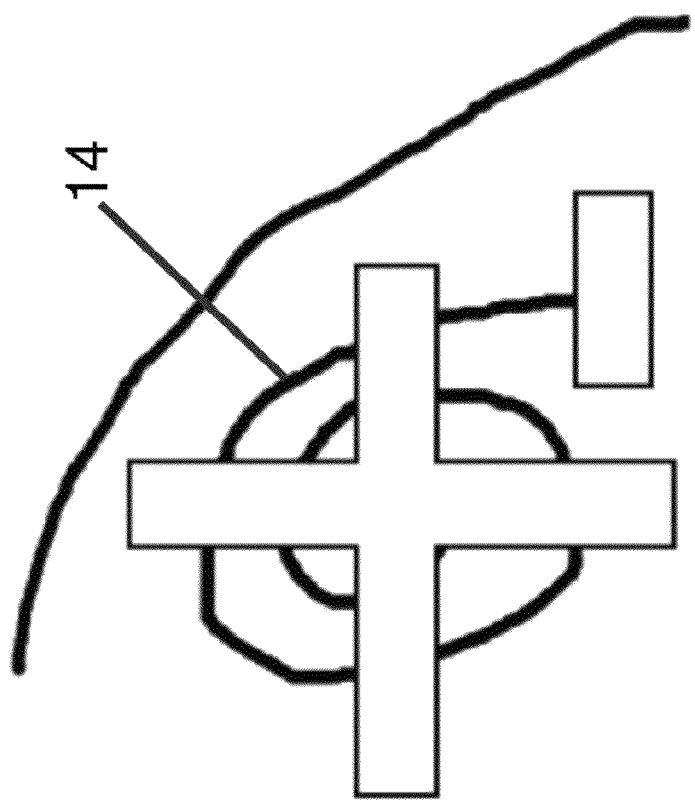
FIG. 1A is a view of the prior art for securing the wire to ensure that it does not move nor cuts anyone.

In surgery for the abnormal area the doctor will follow the wire 14 to the location of the abnormal area. FIG. 1A shows the current method for dealing with the wire before surgery to remove the abnormal area. Basically in this method gauzes are placed over the sharp end of the wire 14. Then the gauzes and wire 14 are attached to the skin by tape to hold them in place. The tape usually causes irritation for the patient and does not adequately secure the wire 14.

Figure 2:
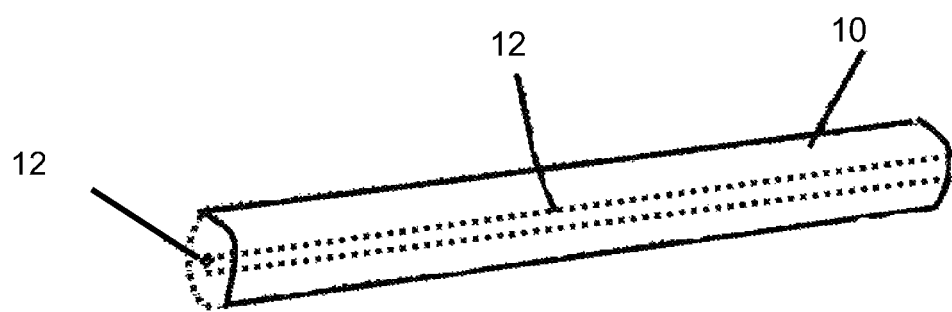
FIG. 2 is a perspective view of one of the devices of the invention. The device is used to cover the wire.

FIG. 2 shows the first device of three devices of the invention. FIG. 2 is a perspective view of this device. The first device is a piece of small diameter latex free radiolucent flexible tubing 10. The flexible tubing 10 has a small diameter opening 12 running through its center. One of the ends of the flexible tubing 10 can be closed. The tubing 10 is placed over the wire 14 that had been inserted by the doctor locating the abnormal area for the biopsy. The tubing 10 is of sufficient length that it will fully cover the whole wire 14. Thus, the tubing 10 covers the sharp end of the wire 14.

Figure 3:
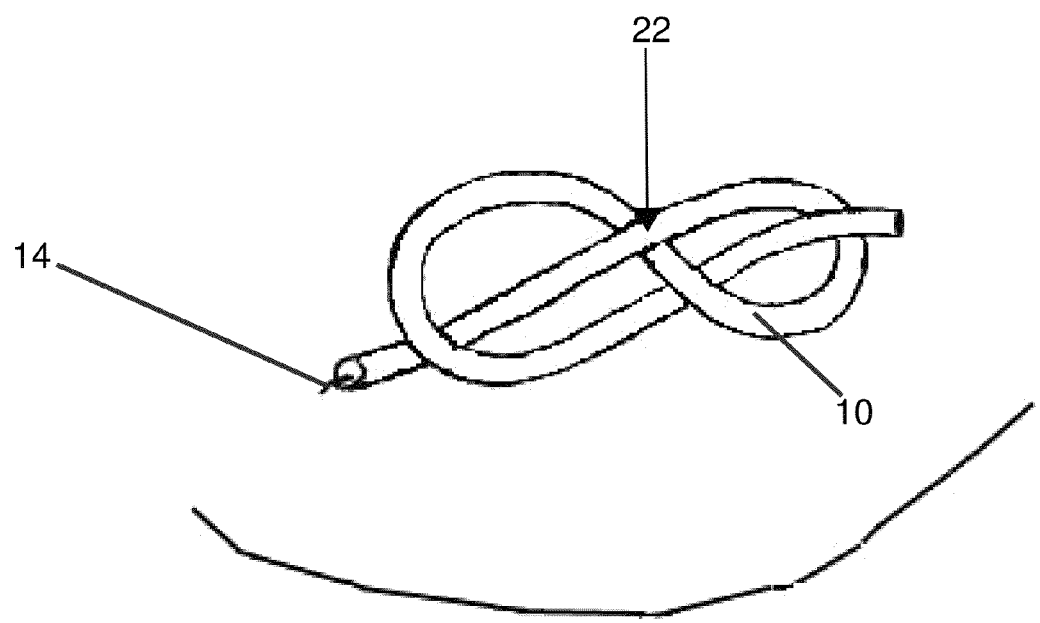
FIG. 3 is a view of the first device loosely looped in a circle.
Figure 4:
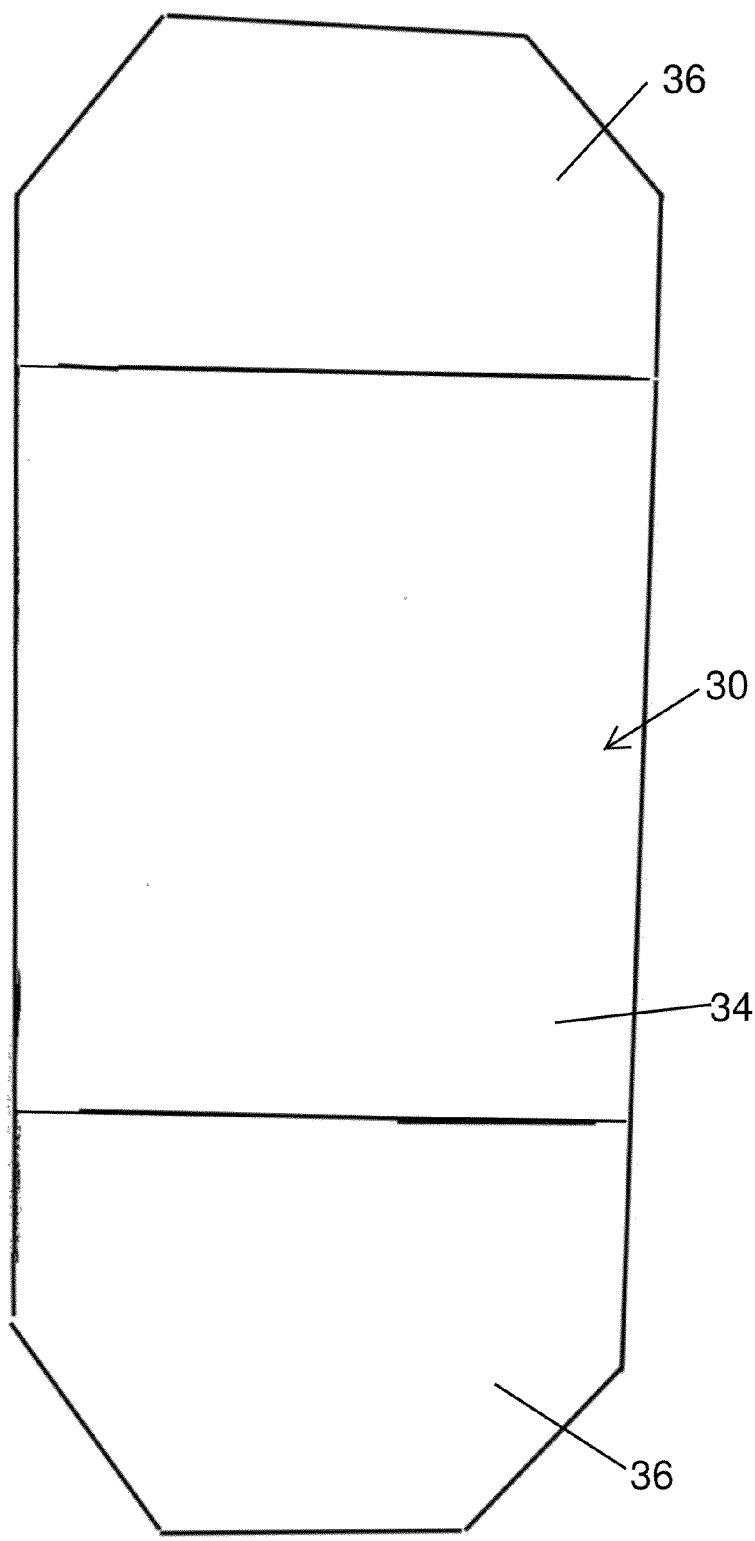
FIG. 4 is a view of another of the devices of the invention. The device is used to secure the wire to the patient.

Once the wire has been fully covered by the tubing 10, the tubing 10 is looped in a loose circle 22. This is shown on in FIG. 3. FIG. 3 shows the tubing 10 looped in a loose circle 22. FIG. 4 shows one embodiment of the second device 30. The second device 30 is a rectangular piece of non-latex material. On each end 36 of the non-latex material 30 a latex free adhesive is placed. The center 38 of the material has no adhesive. The center 38 of the piece of material 34 is placed over the flexible tubing 10 that has been looped into a circle 22. The two ends then are placed against the skin to hold the flexible tubing 10 in place.

Figure 5:
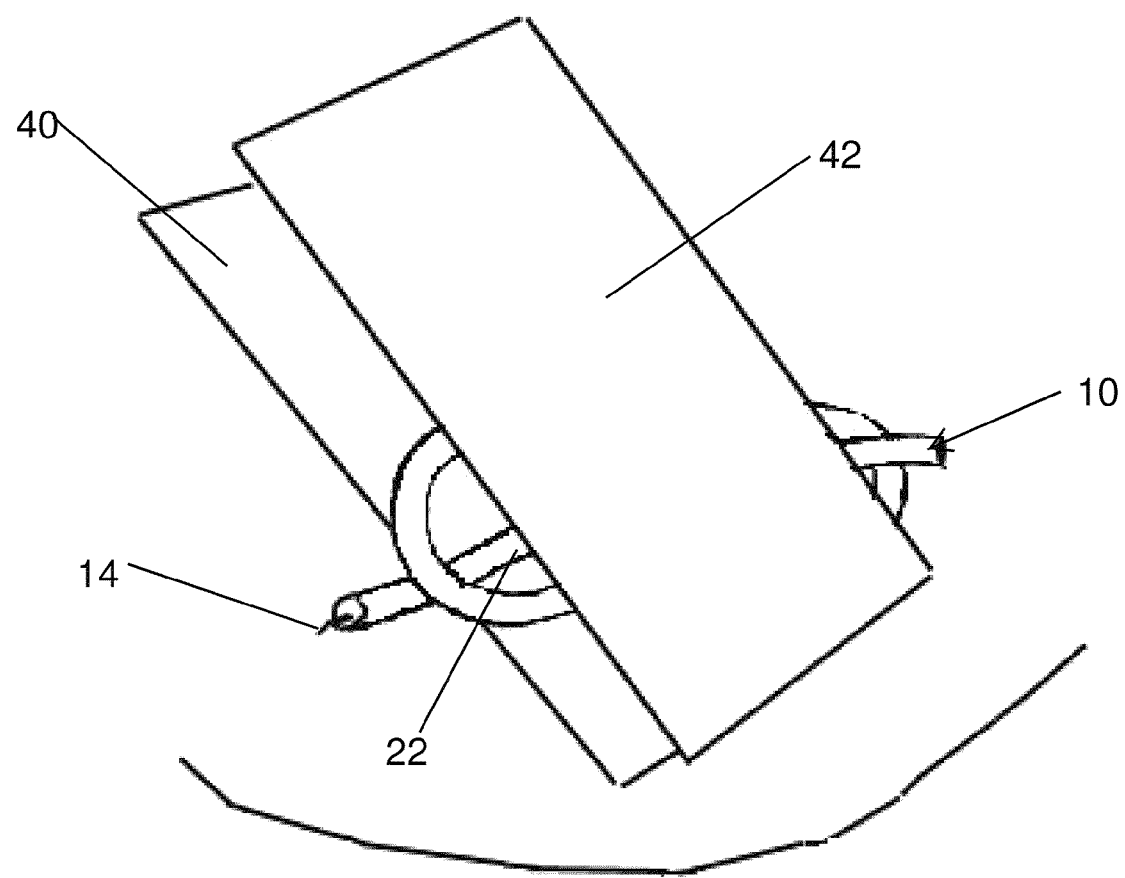
FIG. 5 is a view of another embodiment of the device that is used to secure the wire to the patient.

Another embodiment of the second device is shown in FIG. 5. In this embodiment, the device has two pieces 40 and 42. The first piece 40 is a piece of hook and loop fabric with an adhesive on its back. In this embodiment the hook and loop fabric is pressed on the skin underneath the flexible tubing 10 which is in a formed of a circle 22. A second piece 42 of hook and loop fabric of a different type from the hook and loop fabric of 40 then is placed over the flexible tubing 10 in the form of the circle 22 and pressed against the first piece 40. The two pieces of hook and loop fabric 40 and 42 hold the flexible tubing 22 in place.

Figure 6:
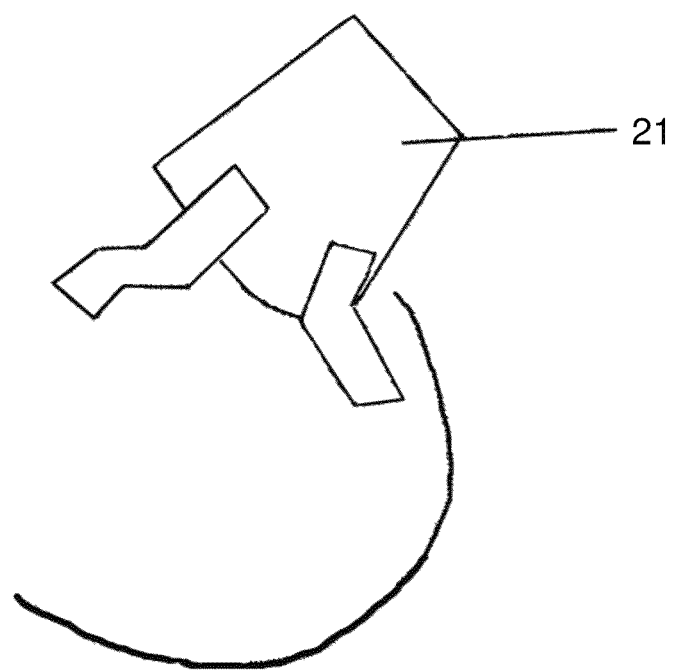
FIG. 6 is a view of the prior art to secure the wire and needle when the doctor leaves both the wire and needle in the patient while waiting for surgery.

The doctor may leave the needle and wire in the breast prior to surgery. This needs to be secured to protect the needle from becoming accidentally displaced or from injuring the patient with the sharp edges. The needle and wire 14 again protrudes from the skin. The needle and wire 14 need to be covered until the patient is moved into the surgical suite and surgery begins. FIG. 6 shows the prior art which is used to protect the needle and wire 14 and the surgery patients while they are waiting for surgery. FIG. 6 shows a Dixie cup 21 has been placed over the needle and wire 14 and Dixie cup 21 has been taped to the skin. The use of Dixie cups 21 brings up many medical issues and many patients are allergic to tape or the adhesive on the tape.

Figure 7:
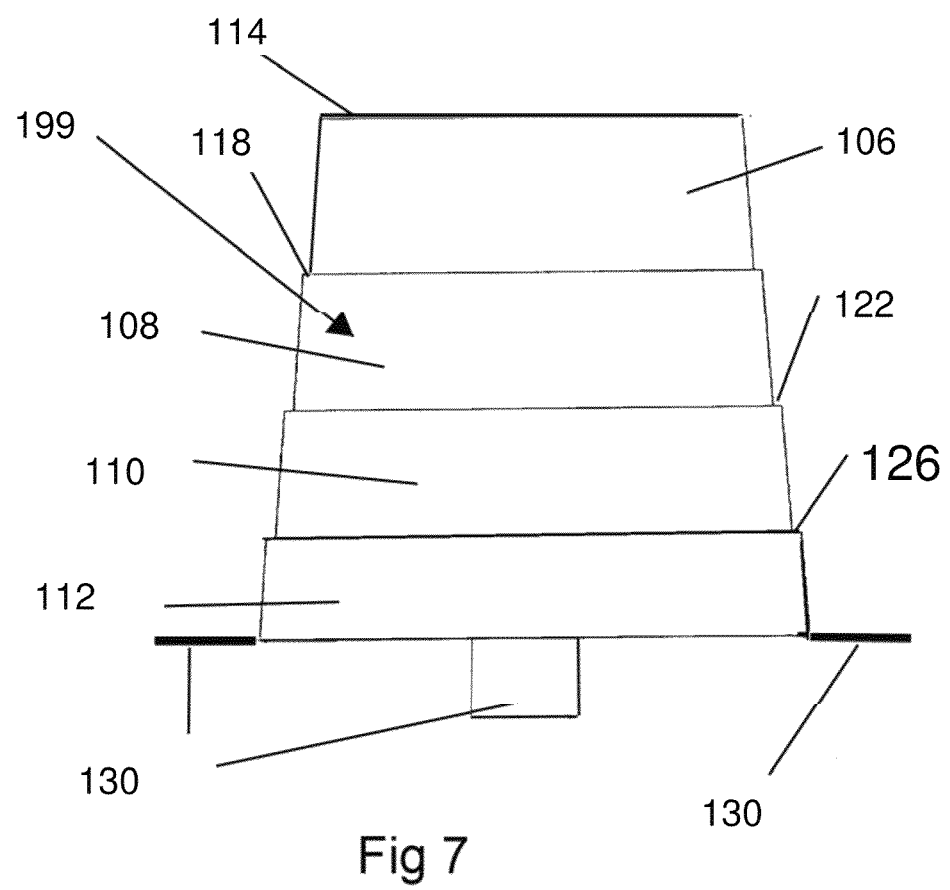
FIG. 7 is a view of the third device (the cup like device) being used to secure the wire and needle when the needle location is completed.
Figure 8:
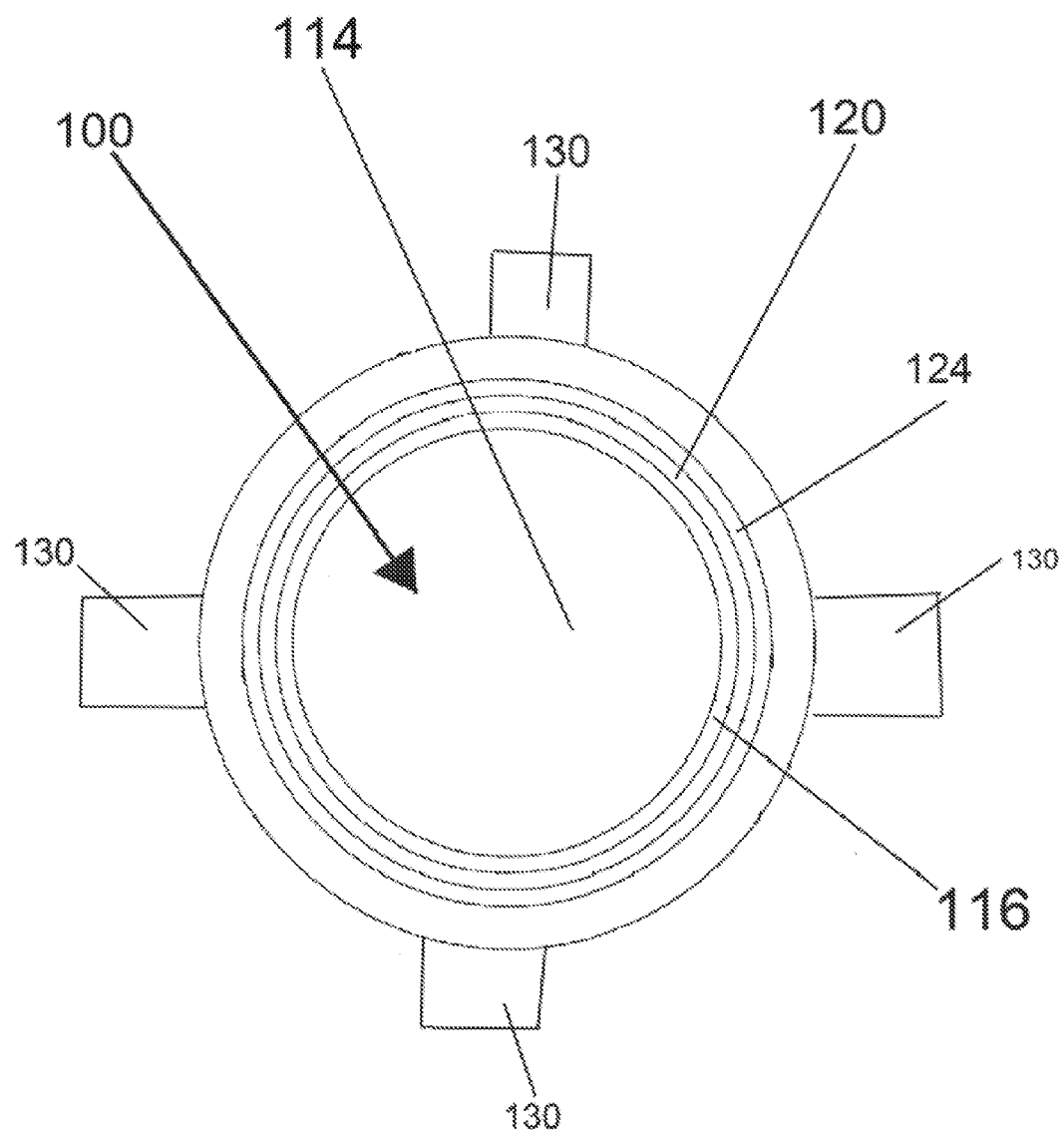
FIG. 8 is a top view of the third device showing the four parts of the expandable cup.

FIG. 7 shows the invention and use on the patient. FIG. 7 shows, an expandable cup 100 that has been placed over the needle and wire 14 of FIG. 5. The expandable cup has four tabs 104. These tabs 104 have adhesive on their bottom and are used to hold the cup 100 on the skin. FIG. 8 shows a top view of the expandable cup 100. The expandable cup 100 is made of four cylindrical pieces 106, 108, 110, and 112. The expandable pieces 106, 108, 110, and 112 are interlocking which enables the expandable cup 100 to expand. In the preferred embodiment piece 106 has an enclosed top 114. At the bottom and on the outside of the cylindrical surface of piece 106 is a ridge 116. Piece 108 is cylindrical with an open bottom and top. At piece 108's top and on the inside of its cylindrical surface is a ridge 118. At the bottom of piece 108 and on the outside of the cylindrical surface is another ridge 120. Pieces 106 and 108 interlock. Piece 106 is slightly smaller in diameter than piece 108. Piece 108 fits over piece 106 and ridge 116 at the bottom of piece 106 and ridge 118 at the top of piece 108 make contact with each other when the cup is expanded. The inner diameter of ridge 118 is nearly the same as the outer diameter of piece 106 so that the friction between the ridge 118 and piece 106 will hold the cup in the expanded position.

Piece 108 is slightly smaller in diameter than piece 110. Piece 108 fits inside piece 110. Piece 110 has an open bottom and top. Piece 110 at its top has a ridge 122 on the inside of its cylindrical surface. Piece 110 has a second ridge 124 on its outside at the bottom. Piece of 108 fits inside piece 110 and the ridge 120 at the bottom of piece 108 and the ridge 122 at the top of piece 110 make contact with each other when the cup is expanded. The inner diameter of ridge 122 is nearly the same as the outer diameter of piece 108 so that the friction between the ridge 122 and piece 108 will hold the cup in the expanded position.

Piece 110 is slightly smaller in diameter than piece 112. Piece 110 fits inside piece 112. Piece 112 has an open bottom and top. Piece 112 at its top has a ridge 126 on the inside of its cylindrical surface. Piece of 110 fits inside piece 112 and the ridge 124 at the bottom of piece 110 and the ridge 126 at the top of piece 112 make contact with each other when the top is expanded. The inner diameter of ridge 126 is nearly the same as the outer diameter of piece 110 so that the friction between the ridge 126 and piece 110 will hold the cup in the expanded position.

On the outer wall of piece 112 at its top are four tabs 130. These four tabs 130 are on their bottom are covered with a non allergic latex free adhesive. The tabs are used to secure the expandable cup 100 that has been placed over the needle and wire 12. The patient is now protected from being injured by the needle and wire 12

Figure 9:
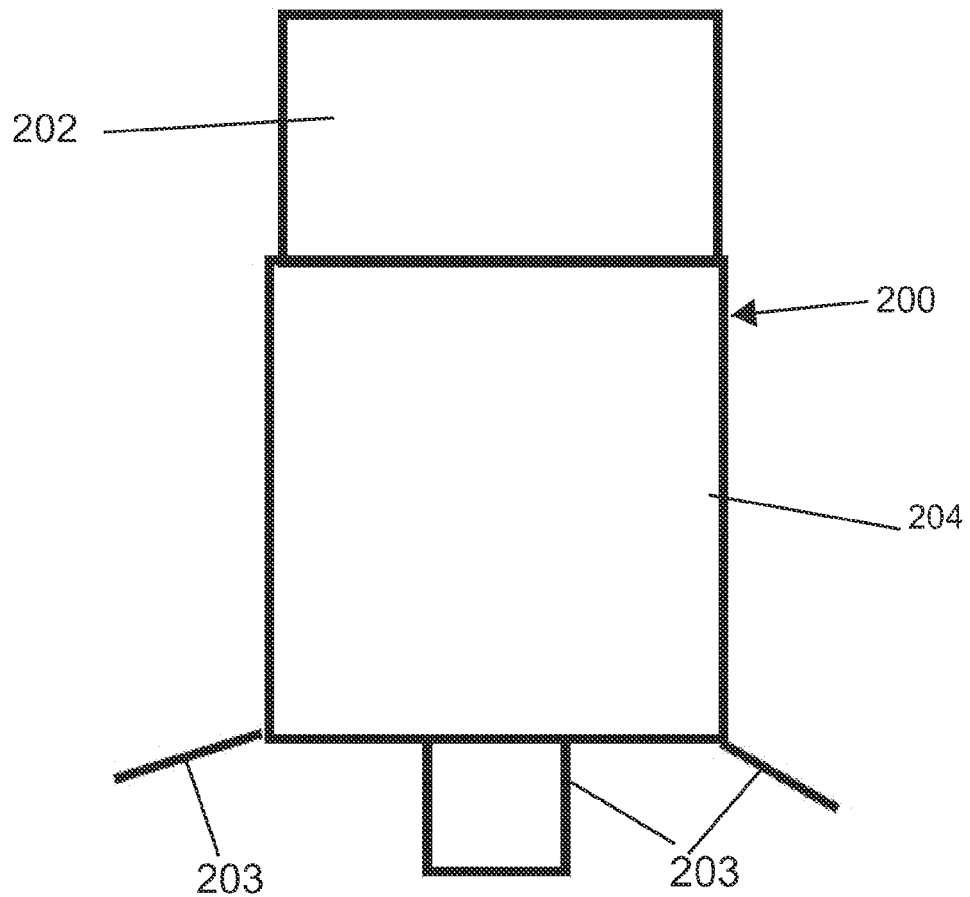
FIG. 9 is another embodiment of the third device (the cup like device) being used to secure the wire and needle when the needle location is completed.
Figure 9A:
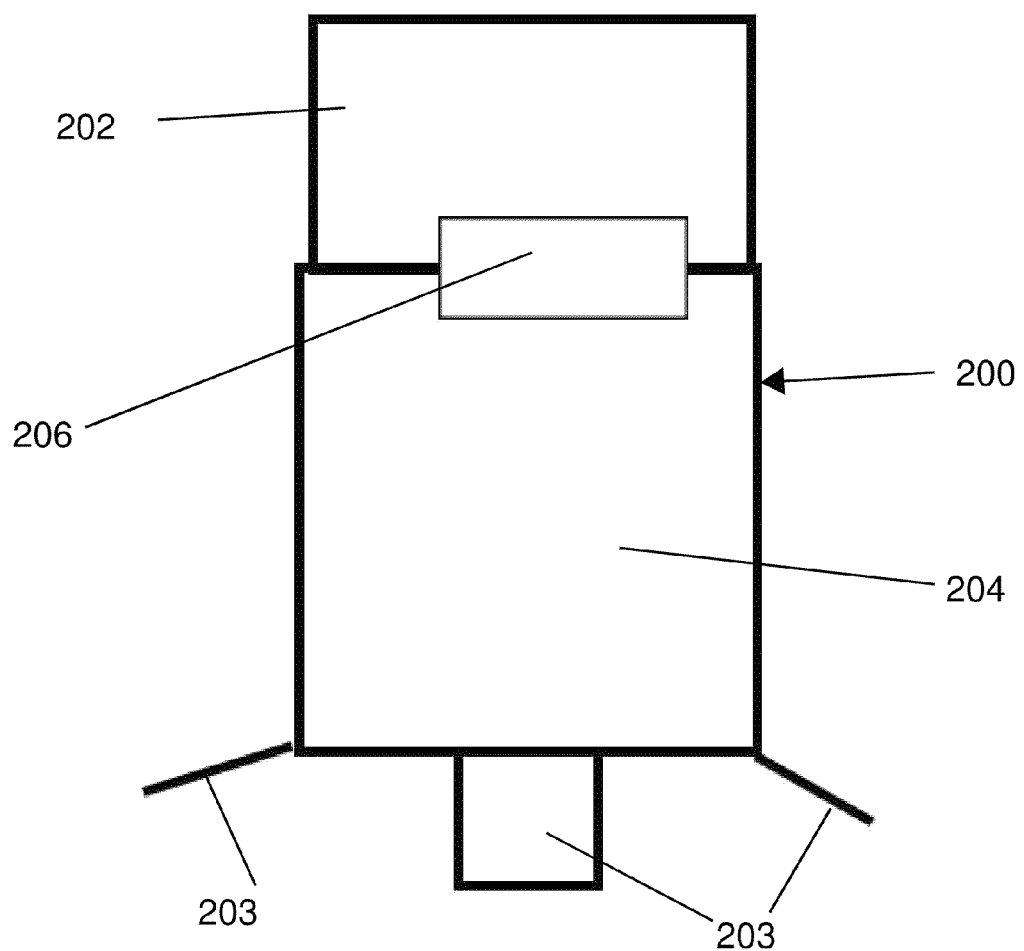
FIG. 9A is the embodiment of FIG. 9 with a piece of tape used to hold the sections in place.

FIG. 9 shows another embodiment of the expandable cup 200. In this embodiment the expandable cup only has two sections. The cup 200 is made with two sections 202 and 204. In the preferred embodiment these section 202 and 204 are cylindrical, however they could be rectangular or any other sided prismatoid whose base is polygonal. The top section 202 outer perimeter nearly the same as the inter perimeter of bottom section 204. Top section 202 fits within bottom section 204. Top section 202 can be moved up and down in bottom section 204. The friction of top section 202 outer perimeter on bottom section 204 inner perimeter hold top section 202 in place. Further a piece of surgical tape 206 can be placed around the boundaries of top section 202 to hold it in place as shown in FIG. 9A.

As in the previous embodiment the cup 200 has four tabs 203. These tabs 203 are equally spaced around the parameter of the cup 200. These four tabs 203 on their bottom are covered with a non allergic latex free adhesive. The tabs are used to secure the expandable cup 200 that has been placed over the needle and wire 12. The patient is now protected from being injured by the needle and wire 12.

Figure 10:
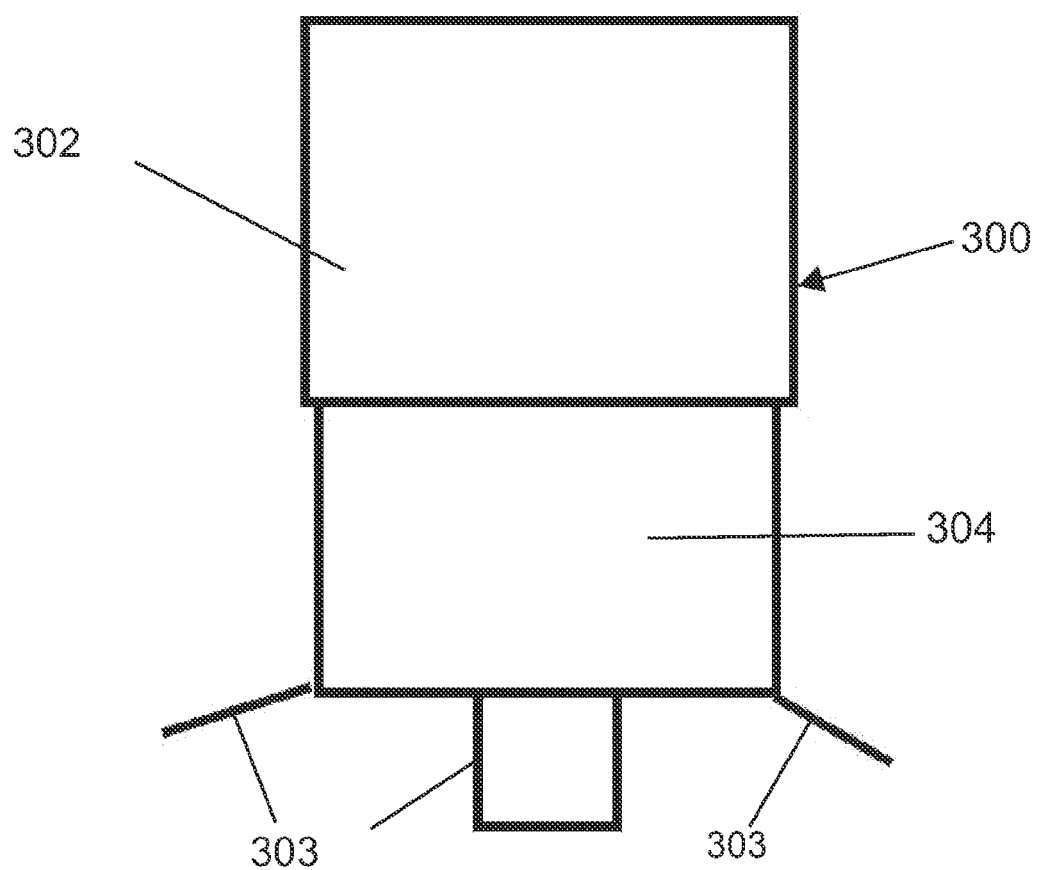
FIG. 10 is another embodiment of the third device (the cup like device) being used to secure the wire and needle when the needle location is completed.
Figure 10A:
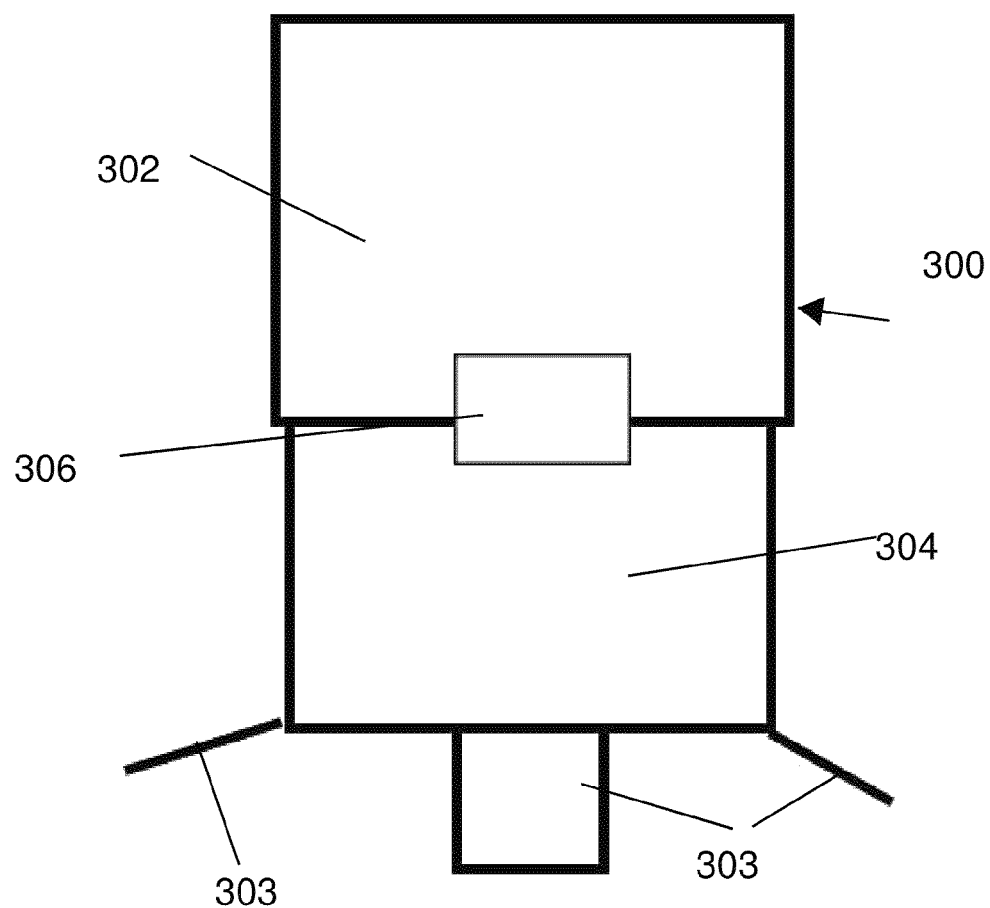
FIG. 10A is the embodiment of FIG. 10 with a piece of tape used to hold the sections in place.

FIG. 10 shows another embodiment of the invention. This embodiment is exactly as the pervious embodiment except the top section 302 fits over the bottom section 304. As in the previous embodiment Top section 302 can be moved up and down on bottom section 304. The friction of top section 302 inner perimeter on bottom section 304 outer perimeter hold top section 302 in place. Further a piece of surgical tape 306 can be placed around the boundaries of top section 302 to hold it in place as shown in FIG. 10A.

As in the previous embodiment the cup 300 has four tabs 303. These tabs 303 are equally spaced around the parameter of the cup 300. These four tabs 303 on their bottom are covered with a non allergic latex free adhesive. The tabs are used to secure the expandable cup 300 that has been placed over the needle and wire 12. The patient is now protected from being injured by the needle and wire 12.

I claim:

1. A method for securing a portion of a wire protruding from a patient who had undergone mammography or ultrasound guided needle localization and is waiting for surgery comprising the steps of:
   a. threading a flexible tube with a small opening that runs through the center of the flexible tube over the portion of the wire used in mammography or ultrasound guided needle localization protruding from the patient,
   b. stopping the threading of the flexible tube when the flexible tube has covered only the portion of the wire protruding from the patient,
   c. configuring the flexible tube containing the wire protruding from the patient in a loose loop for securing the flexible tube containing the wire protruding from the patient to the patient,
   d. configuring a bandage to secure the loose loop in the patient.

2. A method for securing a portion of a wire protruding from a patient who had undergone mammography or ultrasound guided needle localization and is waiting for surgery as in claim 1 further comprising the steps of:
   a. the configuring of the bandage to secure the loose loop is by placing an adhesive bandage over the flexible tube containing the wire protruding from the patient configured in a loose loop for securing the loose loop to the patient.

3. A method for securing a portion of a wire protruding from a patient who had undergone mammography or ultrasound guided needle localization and is waiting for surgery as in claim 2 wherein:
   a. the bandage is latex free.

4. A method for securing a portion of a wire protruding from a patient who had undergone mammography or ultrasound guided needle localization and is waiting for surgery as in claim 3 wherein:
   a. the adhesive bandage has two ends with adhesive only on its two ends and the adhesive bandage has a central area without adhesive that is placed over the loose loop and the ends of the adhesive bandage has adhesive that is adapted for securing the ends to the patient and the central area is adapted for securing the flexible tube configured in a loose loop security against the patient.

5. A method for securing a portion of a wire protruding from a patient who had undergone mammography or ultrasound guided needle localization and is waiting for surgery as in claim 1 wherein;
   a. the tube completely covers the wire protruding from the patient.

6. A method for securing a portion of a wire protruding from a patient who had undergone mammography or ultrasound guided needle localization and is waiting for surgery as in claim 5 wherein;
   a. the flexible tube is radiolucent and latex free.

7. A method for securing a portion of a wire protruding from a patient who had undergone mammography or ultrasound guided needle localization and is waiting for surgery as in claim 1 wherein:
   a. the configuring of the bandage to secure the loose loop comprises the steps of;
      (1.) configuring a first piece of hook and loop fabric with a top and bottom with an adhesive on the bottom and the hook and loop fabric on the top for placing on the patient under the loop of flexible tubing and the adhesive on the bottom of the first piece of hook and loop fabric is configured to attach to the patient;
      (2.) laying the loop of flexible tubing on top of the first piece hook and loop fabric;
      (3.) placing a second piece of hook and loop fabric with a top and bottom with hook and loop fabric of a type opposite the hook and loop fabric of the first piece and said hook and loop fabric is on the bottom of the second piece, on top of the first piece of hook and loop fabric and the loop of flexible tubing and pressing the second piece of hook and loop fabric against the first piece of hook and loop fabric which holds the loop of flexible tubing in place.

8. A patient safety and wellbeing device for covering a needle protruding from a patient used in mammography or ultrasound guided needle localization comprising;
   a. a first container with an open top and open bottom and an inner surface that is of sufficient size to fit around the needle place within a patient;
   b. a second container with an open bottom;
   c. said second container can be moved up and down and is held in place by friction with the first container;
   d. tabs with a bottom that protrude from the bottom of the first container;
   e. said tabs protrude outwardly and have an adhesive on their bottoms;
   f. said second container fits within said first container;
   g. the top of the first container has a ridge on the inner surface;
   h. the bottom of the second container has a ridge on its outer surface;
   i. when the second container moves upward within the first container the ridge on the top of the first container makes contact with the ridge on the bottom of the second container holding the second container within the first container;
   j. one container's ridge makes contact with the other container's surface and the friction between the ridge and container holds the container in place.

9. A patient safety and wellbeing device for covering a needle protruding from a patient used in mammography or ultrasound guided needle localization as in claim 8 wherein;
   a. both containers' ridges make contact with the other containers' surfaces and the friction between the ridges and containers will hold the containers in place.

10. A patient safety and wellbeing device for covering a needle protruding from a patient used in mammography or ultrasound guided needle localization comprising;
    a. a first container with an open top and open bottom and an inner surface that is of sufficient size to fit around the needle's tip protruding from the patient;
    b. a second container with an open bottom;
    c. said second container can be moved up and down and is held in place by friction with the first container;
    d. the second container has an open top;
    e. a third container with an open bottom place inside the second container;

f. said third container can be moved up and down and is held in place by friction.

11. A patient safety and wellbeing device for covering a needle protruding from a patient used in mammography or ultrasound guided needle localization as in claim 10 further comprising;
   a. a piece of tape is placed on both the first container and the second container such that the containers are held in place.

12. A patient safety and wellbeing device for covering a needle protruding from a patient used in mammography or ultrasound guided needle localization as in claim 10 wherein;
   a. the top of the second container has a ridge on the inner surface;
   b. the bottom of the third container has a ridge on its outer surface;
   c. when the third container moves upward within the second container the ridge on the top of the second container makes contact with the ridge on the bottom of the third container holding the third container within the second container;
   d. one container's ridge makes contact with the other container's surface and the friction between the ridge and container holds the container in place.

13. A method to ensure patient safety and wellbeing while covering a needle protruding from a patient used in mammography or ultrasound guided needle localization as in claim 10 comprising the step of:
   a. placing the device over the needle protruding from a patient;
   b. configuring the adhesive tabs for pressing down against the patient to ensure the device will be attached firmly to the patient;
   c. raising the second and third container to a point where the device fully covers the needle.

14. A method to ensure patient safety and wellbeing while covering a needle protruding from a patient used in mammography or ultrasound guided needle localization using a device encompassing a first container with an open top and open bottom and an inner surface that is of sufficient size to fit around the needle protruding from the patient; a second container with an open bottom; said second container can be moved up and down and is held in place by friction with the first container; tabs with a bottom that protrude from the bottom of the first container; said tabs have an adhesive on their bottoms for attaching the patient safety and wellbeing device to the patient, comprising the steps of:
   a. placing the device over the needle protruding from a patient;
   b. configuring the adhesive tabs for pressing down against the patient to ensure the device will be attached firmly to the patient;
   c. raising the second container to a point where the device fully covers the needle.

15. A method to ensure patient safety and wellbeing while covering a needle protruding from a patient used in mammography or ultrasound guided needle localization as in claim 14 comprising the additional step of:
   a. placing a piece of tape over the first and second container to hold the first and second container in place.

\* \* \* \* \*